United States Patent [19]
Hainaut et al.

[11] 3,958,005
[45] May 18, 1976

[54] TETRAHYDROFURAN DERIVATIVES

[75] Inventors: Daniel Hainaut, Villemomble; Jean-Pierre Demoute, Montreuil-sous-Bois; Pierre Girault, Paris, all of France

[73] Assignee: Roussel Uclaf, Paris, France

[22] Filed: Feb. 3, 1975

[21] Appl. No.: 546,454

[30] Foreign Application Priority Data
Feb. 13, 1974  France ................................ 74.04817

[52] U.S. Cl. ............................. 424/285; 260/347.5; 260/347.4
[51] Int. Cl.² ...................................... C07D 307/28
[58] Field of Search ...................... 260/347.4, 347.5; 424/285

[56] References Cited
UNITED STATES PATENTS
2,551,767   5/1951   Shechter et al. .................. 260/347.5

*Primary Examiner*—Harry I. Moatz
*Attorney, Agent, or Firm*—Hammond & Littell

[57] ABSTRACT

Novel tetrahydrofuran derivatives of the formula

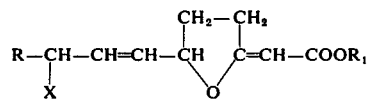

wherein R is a branched or linear alkyl of 1 to 10 carbon atoms and $R_1$ is alkyl of 1 to 5 carbon atoms and X is selected from the group consisting of chlorine, bromine, —OH and alkylcarbonyloxy of 2 to 5 carbon atoms useful as insecticides and their preparation.

11 Claims, No Drawings

TETRAHYDROFURAN DERIVATIVES

OBJECTS OF THE INVENTION

It is an object of the invention to provide the novel tetrahydrofuran derivatives of formula I.

It is another object of the invention to provide a novel process for the preparation of the compounds of formula I.

It is a further object of the invention to provide novel insecticidal compositions and a novel method of killing insects.

These and other objects and advantages of the invention will become obvious from the following detailed description.

THE INVENTION

The novel tetrahydrofuran compounds of the invention have the formula

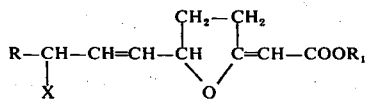

wherein R is a branched or linear alkyl of 1 to 10 carbon atoms and $R_1$ is alkyl of 1 to 5 carbon atoms and X is selected from the group consisting of chlorine, bromine, —OH and alkylcarbonyloxy of 2 to 5 carbon atoms.

Examples of R are alkyl radicals such as methyl, ethyl, isopropyl, propyl, butyl, isobutyl, pentyl, isopentyl, hexyl, isohexyl, heptyl, isoheptyl, octyl, isooctyl, nonyl or decyl. $R_1$ may be a branched or straight chain alkyl such as methyl, ethyl, propyl, isopropyl, butyl, isobutyl, tert.-butyl, pentyl or isopentyl. X may be chlorine, bromine, hydroxy or alkylcarbonyloxy such as acetoxy, propionyloxy, butyryloxy or pentanoyloxy.

A preferred group of compounds are those where R is alkyl of 2 to 8 carbon atoms, $R_1$ is linear alkyl of 1 to 3 carbon atoms and X is chlorine, hydroxy or acetoxy.

The novel process of the invention for the preparation of the compounds of formula I comprises reacting an acid agent with a compound of the formula

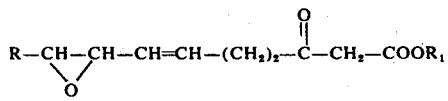

where R and $R_1$ have the above definitions to form a compound of the formula

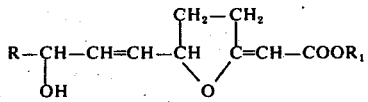

which may then be reacted with a chlorination or bromination agent to form the corresponding halogenated compound of formula I or with an acylation agent to form the corresponding compound of formula I wherein X is alkylcarbonyloxy.

The acid agent for reaction with the compound of formula II may be an aqueous acid agent such as hydrochloric acid, hydrobromic acid, sulfuric acid, nitric acid or trifluoroacetic acid or other acids such as p-toluenesulfonic acid, an ion exchange resin in the acid form or a Lewis acid.

The halogenating agents are preferably thionyl chloride or thionyl bromide but may also be a phosphorus bromide or chloride such as phosphorus trichloride or phosphorus pentabromide. The acylation agent is preferably an acyl chloride such as acetyl chloride or propionyl chloride but may also be other known reagents such as an acyl bromide or acid anhydride.

The compounds of formula II may be prepared by the process described in French Pat. No. 2,085,652 which is illustrated in the example.

The presence of the double bonds in the compounds of formula I means that the compounds may be in the form of their E isomer or Z isomer or mixtures thereof which can be separated, if desired, by known methods such as chromatography.

The novel insecticidal compositions of the invention are comprised of an insecticidally effective amount of at least one compound of formula I and a carrier and optionally one or more other pesticides. The compositions may be in the form of powders, granules, suspensions, emulsions, solutions for aerosols, baits or other preparations usually used for this purpose.

Besides the active principal, the compositions generally contain a vehicle and/or a non-ionic surface active agent to ensure a uniform dispersion of the substances making up the composition. The vehicle may be a liquid such as water, alcohol, hydrocarbons or other organic solvents or animal, vegetable or mineral oils or a powder such as talc, clays, silicates, kieselguhr, etc. The compositions may contain 0.001 to 15%, preferably 0.005 to 5%, by weight of the active material of formula I.

The compositions possess remarkable insecticidal properties and are especially active against eggs, larvae and pupae but are also effective against adult insects. When insect larvae are treated, the larvae evolution is incomplete and usually result in giant larvae possessing malformations and not generally ending in a normal adult form. In the exceptional circumstances in which the larvae matures into a normal appearing adult, the insect is sterile. Examples of insects tested are eggs and larvae of Dysdercus intermedius, nymphs of *Tenebrio molitor* and larvae of *Aedes aegypti*.

The novel method of combatting insects of the invention comprises contacting the insects with an insecticidally effective amount of at least one compound of formula I. The contact may be topically or by ingestion.

In the following examples there are described several preferred embodiments to illustrate the invention. However, it should be understood that the invention is not intended to be limited to the specific embodiments.

EXAMPLE 1

2-(3'-hydroxy-1'-octenyl)-5-(ethoxycarbonylmethine)-tetrahydrofuran

A mixture of 8 g of ethyl 3-oxo-trans 8,9-epoxy cis 6-tetradecenoate, 50 ml of acetone and 20 ml of 2 N hydrochloric acid was stirred for 16 hours at room temperature and the mixture was then poured into water and extracted with methylene chloride. The organic extracts were washed with water, dried and evaporated to dryness. The residue was chromatographed over silica and was eluted with a 6–4 methylene chloride-ethyl acetate mixture to obtain 3 g of 2-(3′-hydroxy-1′-octenyl)-5-(ethoxycarbonylmethine)-tetrahydrofuran wit a refractive index of $n_D^{30} = 1.4860$. IR Spectrum (chloroform): C=O at $1695–1724^{cm-1}$, C=C at $1642^{cm-1}$, OH at $3604^{cm-1}$, cyclic C—O—C and conjugated ester.

EXAMPLE 2

2-(3′-hydroxy-1′-pentenyl)-5-(ethoxycarbonylmethine)-tetrahydrofuran

STEP A: ethyl 3-oxo-8-hydroxy-9-chloro-6-undecynoate 42.2 ml of 1.4 N butyl lithium in hexane were added with stirring to a solution of 10 g of ethyl γ-propargyl-β-ethoxy-crotonate in 75 ml of tetrahydrofuran cooled to −60°C and after holding the mixture at the said temperature for 2 hours, 6.5 g of α-chlorobutyraldehyde were added thereto. The mixture was held at −60°C for 1 hour and after raising the temperature to 0°C a mixture of 90 g of monosodium phosphate in 110 ml of water was added thereto. The mixture was decanted and the aqueous phase was extracted with ethyl acetate. The extracts were washed with a saturated sodium bicarbonate solution, then with water, was dried and evaporated to dryness. The oil residue was mixed with stirring with 120 ml of ethanol and 60 ml of 2 N hydrochloric acid for 16 hours and was then poured into water. The mixture was extracted with methylene chloride and the extracts were washed with water, dried and evaporated to dryness. The oily residue was chromatographed over silica and was eluted with a 3–1 cyclohexane-ethyl acetate mixture to obtain 5.8 g of ethyl 3-oxo-8-hydroxy -9-chloro-6-undecynoate with a refractive index of $n_D^{22} = 1.4855$.

STEP B: ethyl 3-oxo-8-hydroxy-9-chloro cis-6-undecenoate

A solution of 4.6 g of the product of Step A in 66 ml of ethyl acetate containing 0.5 g of 5% palladium on barium sulfate and 0.625 ml of quinoline was hydrogenated and then was filtered to remove the catalyst. The filtrate was washed with dilute hydrochloric acid and then with water, was dried and evaporated to dryness to obtain 4.6 g of ethyl 3-oxo-8-hydroxy-9-chloro-cis-6-undecenoate with a refractive index of $n_D^{20} = 1.4800$.

STEP C: ethyl 3-oxo-8,9-epoxy cis-6-undecenoate 32.8 ml of a solution of 5.8 g of potassium tert.-butylate in 50 ml of tert.-butanol were added at 25°–30°C to a solution of 4.4 g of the product of Step B in 50 ml of tert.-butanol and the mixture was stirred for 3 hours and was then poured into a mixture of 64 g of monosodium phosphate in 160 ml of water. The mixture was decanted and the aqueous phase was extracted with ethyl acetate. The extracts were washed with water, dried and evaporated to dryness to obtain 2.7 g of ethyl 3-oxo-8,9-epoxy cis-6-undecenoate with a refractive index of $n_D^{21} = 1.4850$.

STEP D: 2-(3′-hydroxy-1′-pentenyl)-5-(ethoxycarbonylmethine)-tetrahydrofuran 44 mg of p-toluene sulfonic acid were added to a mixture of 884 mg of the product of Step C in 50 ml of benzene and the mixture was stirred for 2½ hours and was poured into a saturated sodium bicarbonate solution. The mixture was decanted and the organic phase was washed with water, dried and evaporated to dryness. The residue was chromatographed over silica and was eluted with a 7–3 benzene-ethyl acetate to obtain 325 mg of 2-(3′-hydroxy-1′-pentenyl)-5-(ethoxycarbonylmethine)-tetrahydrofuran.

IR Spectrum (chloroform):
Conjugated ester at $1700^{cm-1}$, C=C at $1646^{cm-1}$ and OH.

EXAMPLE 3

2-(3′-hydroxy-1′-undecenyl)-5-(ethoxycarbonylmethine)-tetrahydrofuran

STEP A: ethyl 3-oxo-8-hydroxy-9-chloro-6-heptadecynoate

A mixture of 59 g of caprinaldehyde, 15 ml of methylene chloride and 52 g of sulfuryl chloride was stirred for 2 hours, refluxed for 1 hour and was then rectified to obtain 34.5 g of α-chlorocaprinaldehyde with a boiling point of 115°C at 12 mm Hg and a refractive index of $n_D^{27} = 1.4460$. A mixture of 11.6 g of the said product, 10 g of ethyl γ-propargyl-β-ethoxy-crotonate and 42.2 ml of butyl lithium were reacted as in Step A of Example 2 to obtain 4.75 g of ethyl 3-oxo-8-hydroxy-9-chloro-6-heptadecynoate with a refractive index of $n_D^{22} = 1.4780$.

STEP B: ethyl 3-oxo-8-hydroxy-9-chloro cis-6-heptadecenoate

A solution of 6.9 g of the product of Step A in 440 ml of ethyl acetate in the presence of 0.6 g of 5% palladized barium sulfate and 0.75 ml of quinoline was hydrogenated and the catalyst was filtered off. The filtrate was washed with dilute hydrochloric acid, then with water, was dried and evaporated to dryness. The residue was chromatographed over silica and was eluted with a 3–1 cyclohexane-ethyl acetate mixture to obtain 5.7 g of ethyl 3-oxo-8-hydroxy -9-chloro cis-6-heptadecenoate with a refractive index of $n_D^{20} = 1.4740$.

STEP C: ethyl 3-oxo-8,9-epoxy cis-6-heptadecenoate

Using the procedure of Step C of Example 2, 5.7 g of the product of Step B and 5.8 g of potassium tert.-butylate were reacted to obtain after chromatography over silica and elution with a 2–1 ether-petroleum ether (B.p. = 35°–70°C) mixture 1.24 g of ethyl 3-oxo-8,9-epoxy cis-6-heptadecenoate with a refractive index of $n_D^{20} = 1.4710$.

STEP D: 2-(3′-hydroxy-1′-undecenyl)-5-ethoxycarbonylmethine)-tetrahydrofuran

A mixture of 2.1 g of the product of Step C in 50 ml of benzene and 84 mg of p-toluene sulfonic acid was stirred for 6 hours and was then poured into a saturated sodium bicarbonate solution. The mixture was decanted and the organic phase was washed with water, dried and evaporated to dryness. The residue was chromatographed over silica and was eluted with a 7–3 cyclohexane-ethyl acetate mixture to obtain 730 mg of 2-(3′-hydroxy-1′-undecenyl)-5-(ethoxycarbonylmethine)-tet-rahydrofuran in the form of a mixture of the E and Z isomers with the double bond fixed in the 5-position.

Analysis: $C_{19}H_{32}O_4$.
Calculated: %C, 70.33; %H, 9.94.

Found: %C, 70.0; %H, 10.1.

Another chromatography separated the isomers.

EXAMPLE 4

2-(3'-chloro-1'-octenyl)-5-(ethoxycarbonylmethine)-tetrahydrofuran 2 ml of thionyl chloride were added at 0°C to a solution of 4.9 g of 2-(3'-hydroxy-1'-octenyl)-5-(ethoxycarbonylmethine)-tetrahydrofuran in 40 ml of ether and the mixture was stirred for 2 hours. 7 ml of pyridine were added thereto followed by 30 ml of water and the mixture was decanted. The organic phase was washed with water, dried and evaporated to dryness. The residue was chromatographed over silica and was eluted with a 6–4 methylene chloride-ethyl acetate mixture to obtain 3.5 g of 2-(3'-chloro-1'-octenyl)-5-(ethoxycarbonylmethine)-tetrahydrofuran with a refractive index of $n_D^{22} = 1.4964$.

Analysis: $C_{16}H_{25}ClO_3$.

Calculated: %C, 63.88; %H, 8.37.

Found: %C, 63.9; %H, 8.6.

EXAMPLE 5

2-(3'-acetoxy-1'-octenyl)-5-(ethoxycarbonylmethine)-tetrahydrofuran 2 ml of acetyl chloride were added to a solution of 2 g of 2-(3'-hydroxy-1'-octenyl)-5-(ethoxycarbonylmethine)-tetrahydrofuran in 25 ml of ether and the mixture was stirred for 16 hours and was then evaporated to dryness. The residue was chromatographed over silica and was eluted with a 6–4 methylene chloride-ethyl acetate mixture to obtain 1.0 g of 2-(3'-acetoxy-1'-octenyl)-5-(ethoxycarbonylmethine)-tetrahydrofuran with a refractive index of $n_D^{25} = 1.4815$.

IR Spectrum (chloroform): C=O and conjugated ester at 1724, 1696 and $1680^{cm-1}$ and C=C at $1636^{cm-1}$.

INSECTICIDAL COMPOSITIONS

An emulsifiable concentrate was prepared from 0.1% by weight of 2-(3'-hydroxy-1'-octenyl)-5-(ethoxycarbonylmethine)-tetrahydrofuran, 5% by weight of Polysorbate 80 [polyoxyethylene (20) sorbitan monooleate], 94.8% by weight of xylene and 0.1% by weight of Topanol A (2,4-dimethyl-6-tert.-butyl-phenol).

Another emulsifiable concentrate was prepared from 0.1% by weight of 2-(3'-chloro-1'-octenyl)-5-(ethoxycarbonylmethine)-tetrahydrofuran, 5% by weight of Atlox 4851 (mixture of alkylaryl sulfonates and polyoxyethylene triglycerides), 5% by weight of Atlox 4855 (mixture of alkylaryl sulfonates and polyoxyethylene triglycerides), 40% by weight of xylene and 49.9% by weight of cyclohexanone.

INSECTICIDAL ACTIVITY

A. *Dysdercus intermedius* larvae and *Tenebrio molitor* nymphs

This test was effected on the larvae in the last stage of their development and the test products were topically applied to the abdominal tergites of the insects at a rate of 5 μl of an acetone solution containing 20 and 2 g/l of the test compound or 100 and 10 μg of the test product. Ten insects were used for each test and at the end of the test, when the control larvae who had received no treatment developed into mature adults, the effects on each treated larvae was noted on a scale of 0 to 5 with 0 corresponding to a normal adult and 5 corresponding to a giant larvae not having been transformed into a normal adult of a second nymph. The intermediate values correspond to the individual having more or less completed growth and having a more or less abnormal form. The following Table reports the averages obtained with each dose and in the case of the control, the values were very near to zero.

TABLE I

| Product of Example | Dysdercus intermedius | | Tenebrio Molitor | |
|---|---|---|---|---|
| | 100 μg | 10 μg | 100 μg | 10 μg |
| 1 | 5 | 0 | 4.8 | 3.8 |
| 2 | 2.7 | 0 | — | — |
| 4 | — | 5 | — | — |
| 5 | 5 | 1.2 | — | — |

B. *Aedes aegypti* larvae

The acetone solutions used in the preceding test were used this time for direct addition to water in which *Aedes aegypti* larvae were being raised and the doses used were 10, 1 and 0.1 ppm of test product. The results were expressed as the percent of dead larvae and for the product of Examples 3 and 4 at 10 ppm, the results were 20% and 100%, respectively.

C. *Dysdercus intermedius* eggs

A piece of filter paper measuring 15 cm × 6 cm was impregnated with an acetone solution of the product of Example 1 corresponding to a dose of 0.1 and 1 g per m² of filter paper surface. The paper sample was then placed in a ring on the inner surface of a beaker containing 2 adult couples of *Dysdercus intermedius* and the eggs laid, fixed on the filter paper were recovered and placed in a hatcher. The percentage of the eggs not hatching was determined for each dose and was 90% at 1 g/m² and 60% at 0.1 g/m².

Various modifications of the products and processes of the invention may be made without departing from the spirit or scope thereof and it is to be understood that the invention is to be limited only as defined in the appended claims.

We claim:

1. A tetrahydrofuran of the formula $$R-CH-CH=CH-CH \underset{X}{\overset{CH_2-CH_2}{\diagdown \diagup}} C=CH-COOR_1$$

wherein R is a branched or linear alkyl of 1 to 10 carbon atoms and $R_1$ is alkyl of 1 to 5 carbon atoms and X is selected from the group consisting of chlorine, bromine, —OH and alkylcarbonyloxy of 2 to 5 carbon atoms.

2. A compound of claim 1 wherein R is linear alkyl of 2 to 8 carbon atoms, $R_1$ is linear alkyl of 1 to 3 carbon atoms and X is selected from the group consisting of chlorine, —OH and acetoxy.

3. A compound of claim 1 which is 2-(3'-hydroxy-1'-octenyl)-5-(ethoxycarbonylmethine)-tetrahydrofuran.

4. A compound of claim 1 which is 2-(3'-hydroxy-1'-pentenyl)-5-(ethoxycarbonylmethine)-tetrahydrofuran.

5. A compound of claim 1 which is 2-(3'-hydroxy-1'-undecenyl)-5-(ethoxycarbonylmethine)-tetrahydrofuran.

6. A compound of claim 1 which is 2-(3'-chloro-1'-octenyl)-5-(ethoxycarbonylmethine)-tetrahydrofuran.

7. A compound of claim 1 which is 2-(3'-acetoxy-1'-octenyl)-5-(ethoxycarbonylmethine)-tetrahydrofuran.

8. An insecticidal composition comprising an insecticidally effective amount of at least one compound of claim 1 and a carrier.

9. The composition of claim 8 wherein R is linear alkyl of 2 to 8 carbon atoms, $R_1$ is linear alkyl of 1 to 3 carbon atoms and X is selected from the group consisting of chlorine, —OH and acetoxy.

10. A method of killing insects comprising applying to insects an insecticidally effective amount of at least one compound of claim 1.

11. The method of claim 10 wherein R is linear alkyl of 2 to 8 carbon atoms, $R_1$ is linear alkyl of 1 to 3 carbon atoms and X is selected from the group consisting of chlorine, —OH and acetoxy.

* * * * *